United States Patent

Seino et al.

Patent Number: 4,943,637
Date of Patent: * Jul. 24, 1990

[54] METHOD FOR PREPARING 2-PHENYLBENZOTRIAZOLES

[75] Inventors: Shuichi Seino, Kobe; Tomizo Fujino, Akashi, both of Japan

[73] Assignee: Chemipro Kasei Kaisha, Ltd., Hyogo, Japan

[*] Notice: The portion of the term of this patent subsequent to May 30, 2006 has been disclaimed.

[21] Appl. No.: 232,567

[22] Filed: Aug. 12, 1988

Related U.S. Application Data

[63] Continuation of Ser. No. 932,457, Nov. 18, 1986, abandoned.

[30] Foreign Application Priority Data

Sep. 16, 1986 [JP] Japan ................... 61-218864
Sep. 16, 1986 [JP] Japan ................... 61-218865

[51] Int. Cl.$^5$ ........................ C07D 249/20
[52] U.S. Cl. ........................ 548/260; 548/259
[58] Field of Search ............ 548/260, 259, 257

[56] References Cited

U.S. PATENT DOCUMENTS 4,642,350 2/1987 Davatz ................... 548/260
4,780,541 10/1988 Seino ................... 548/257
4,835,284 5/1989 Seino ................... 548/260

FOREIGN PATENT DOCUMENTS 170172 9/1984 Japan ................... 548/260
172481 9/1984 Japan ................... 548/260

OTHER PUBLICATIONS

Fieser and Fieser, *Organic Chemistry*, 3rd Ed., (1956: Reinhold Publishing Co., N.Y.), p. 362.

Primary Examiner—Donald G. Daus
Attorney, Agent, or Firm—Felfe & Lynch

[57] ABSTRACT

This invention relates to a method for preparing a 2-phenylbenzotriazole of formula I,

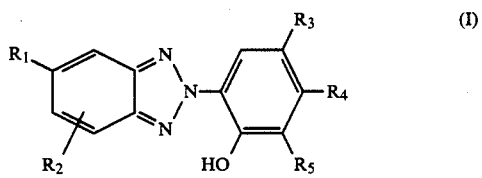

(wherein $R_1$ represents hydrogen or chlorine atom, a lower alkyl group having a carbon number of 1 to 4, a lower alkoxy group having a carbon number of 1 to 4, carboxyl group, or sulfonic acid group; $R_2$ represents hydrogen or chlorine atom, a lower alkyl group having a carbon number of 1 to 4, or a lower alkoxy group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxy group having a carbon number of 1 to 4; and $R_5$ represents hydrogen atom, an alkyl group having a carbon number of 1 to 12, or a phenylalkyl group, the alkyl part of which has a carbon number of 1 to 4), which comprises reducing an o-nitroazobenzene of formula III,

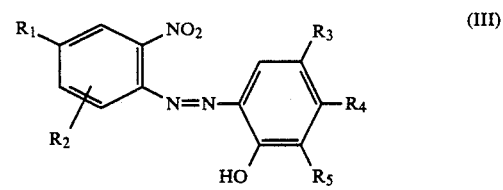

(wherein $R_1$, $R_2$, $R_3$, $R_4$ and $R_5$ are as defined above) with at least one selected from the group consisting of primary and secondary alcohol reducing agents in the presence of an aromatic ketone catalyst and base.

This invention further relates to a method for preparing a 2-phenylbenzotriazole of formula I as defined above, which comprises reducing 1 mole 2-phenylbenzotriazole-N-oxide of formula II,

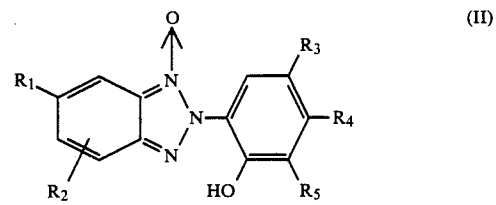

(wherein $R_1$, $R_2$, $R_3$, $R_4$ and $R_5$ are as defined above) with 0.4 to 0.7 mole primary alcohol and/or 0.8 to 1.4 mole secondary alcohol in the presence of an aromatic ketone catalyst and base.

This invention still further relates to a method for preparing a 2-phenylbenzotriazole-N-oxide of formula II as defined above, which comprises reducing 1 mole o-nitroazobenzene of formula III as defined above with 0.4 to 0.7 mole primary alcohol and/or 0.8 to 1.4 mole secondary alcohol in the presence of an aromatic ketone catalyst and base.

18 Claims, No Drawings

METHOD FOR PREPARING 2-PHENYLBENZOTRIAZOLES

This application is a continuation of application Ser. No. 932,457, filed November 18, 1986 now abandoned.

BACKGROUND OF THE INVENTION (a) Field of the Invention

This invention relates to a method for preparing 2-phenylbenzotriazoles having the following general formula I, which are useful as an ultraviolet ray absorber.

This invention further relates to a method for preparing 2-phenylbenzotriazole-N-oxides having the following general formula II, which are a useful intermediate for said 2-phenylbenzotriazoles.

(b) Description of the Prior Art 2-phenylbenzotriazoles having the following general formula I,

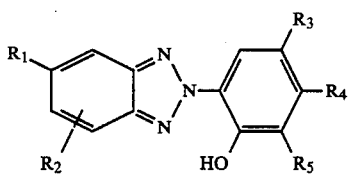

(wherein $R_1$ represents hydrogen or chlorine atom, a lower alkyl group having a carbon number of 1 to 4, a lower alkoxy group having a carbon number of 1 to 4, carboxyl group, or sulfonic acid group; $R_2$ represents hydrogen or chlorine atom, a lower alkyl group having a carbon number of 1 to 4, or a lower alkoxy group having a carbon number of 1 to 4; $R_3$ represents hydrogen or chlorine atom, an alkyl group having a carbon number of 1 to 12, a lower alkoxy group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxy group, or a lower alkoxy group having a carbon number of 1 to 4; and $R_5$ represents hydrogen atom, an alkyl group having a carbon number of 1 to 12, or a phenylalkyl group, the alkyl part of which has a carbon number of 1 to 4) are known to be useful as an ultraviolet ray absorber to be added to plastics, paints, oils and the like.

2-phenylbenzotriazole-N-oxides having the general formula II,

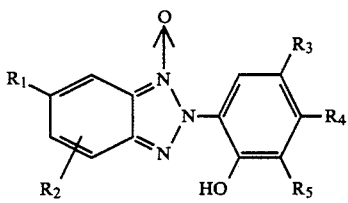

(wherein $R_1$, $R_2$, $R_3$, $R_4$ and $R_5$ are the same as defined above with regard to the general formula I) are known to be an important intermediate for said 2-phenylbenzotriazoles.

Heretofore, these 2-phenylbenzotriazoles and 2-phenylbenzotriazole-N-oxides have been produced by chemically or electrolytically reducing o-nitroazobenzene derivatives having the general formula III,

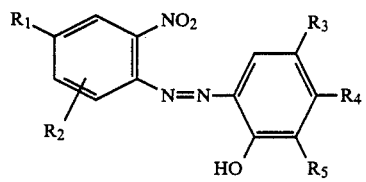

(wherein $R_1$, $R_2$, $R_3$, $R_4$ and $R_5$ are the same as defined above with regard to the general formula I). However, these conventional methods respectively have merits and demerits, and are not always satisfactory.

For example, Japanese Patent Publication No. 37-5934 and U.S. Pat. No. 3,773,751 disclose a method for preparing 2-phenylbenzotriazoles or 2-phenylbenzotriazole-N-oxides by chemically reducing o-nitroazobenzene derivatives in an alcoholic sodium hydroxide solution with zinc powder at a satisfactory yield. However, this sodium hydroxide-zinc system produces zinc sludge which results in waste water contamination problems.

As disclosed in U.S. Pat. No. 2,362,988, ammonium sulfide, alkali-sulfide, zinc-ammonia system, hydrogen sulfide-sodium system and zinc-hydrochloric acid system are used as a chemical reducing agent for the above mentioned reduction reaction. However, this conventional method produces a large amount of sulfite or zinc salts which result in waste water contamination. The sulfite further generates sulfurous acid gas, and the used sulfide type reducing agent generates poisonous hydrogen sulfide, which results in environmental polution problems.

Japanese Patent Laid Open Nos. 51-138679 and 51-138680 disclose a reduction method by the addition of pressurized hydrogen. Japanese Patent Laid Open No. 50-88072 discloses a reduction method by hydrazine. However, these methods are not satisfactory in view of yield and economy, and it is impossible to obtain the desired product of high purity because a side reaction is caused during the main reaction. Particularly, in the case of producing a chlorine-containing product, a side reaction such as dechlorination reaction is caused.

Japanese Patent Laid Open Nos. 59-170172 and 59-172481 disclose our invention relating to a method for reducing o-nitroazobenzene with alcohols in the presence of quinones. However, quinones have dangers to irritate a skin and a mucous membrane and sometimes to cause a rash on a skin. Therefore, great care must be taken in handling the quinone catalyst in such a manner that human skin and mucous membrane may not come into contact with quinones and their vapor. In addition to this disadvantage, the used quinone catalyst changes in quality, and its catalytic ability is lowered. Furthermore, the recovery of the used catalyst is difficult.

SUMMARY OF THE INVENTION

An object of the present invention is to provide a novel method for preparing 2-phenylbenzotriazoles and 2-phenylbenzotriazole-N-oxides, which solves the above mentioned problems of the conventional methods.

(i) That is, an object of the present invention is to provide a method for preparing 2-phenylbenzotriazoles having the general formula I,

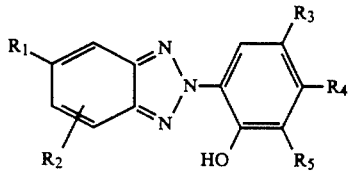

(wherein $R_1$ represents hydrogen or chlorine atom, a lower alkyl group having a carbon number of 1 to 4, a lower alkoxy group having a carbon number of 1 to 4, carboxyl group, or sulfonic acid group; $R_2$ represents hydrogen or chlorine atom, a lower alkyl group having a carbon number of 1 to 4, or a lower alkoxy group having a carbon number of 1 to 4; $R_3$ represents hydrogen or chlorine atom, an alkyl group having a carbon number of 1 to 12, a lower alkoxy group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxy group, or a lower alkoxy group having a carbon number of 1 to 4; and $R_5$ represents hydrogen atom, an alkyl group having a carbon number of 1 to 12, or a phenylalkyl group, the alkyl part of which has a carbon number of 1 to 4), characterized by reducing o-nitroazobenzenes having the general formula III,

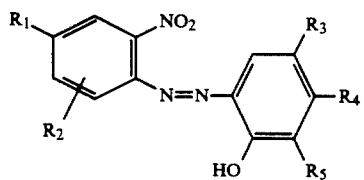

(wherein $R_1$, $R_2$, $R_3$, $R_4$ and $R_5$ are the same as defined above) with at least one of primary alcohols and secondary alcohols in the presence of an aromatic ketone compound catalyst and base.

(ii) Another object of the present invention is to provide a method for preparing 2-phenylbenzotriazoles having the general formula I,

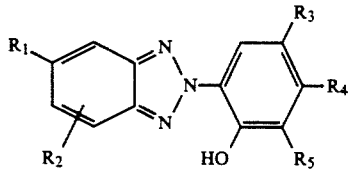

(wherein $R_1$, $R_2$, $R_3$, $R_4$ and $R_5$ are the same as defined above), characterized by reducing 2-phenylbenzotriazole-N-oxides having the general formula II,

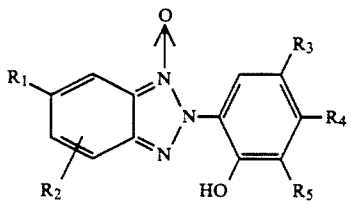

(wherein $R_1$, $R_2$, $R_3$, $R_4$ and $R_5$ are the same as defined above) with at least one of primary alcohols and secondary alcohols in the presence of an aromatic ketone compound catalyst and base.

(iii) Still other object of the present invention is to provide a method for preparing 2-phenylbenzotriazole-N-oxides having the general formula II,

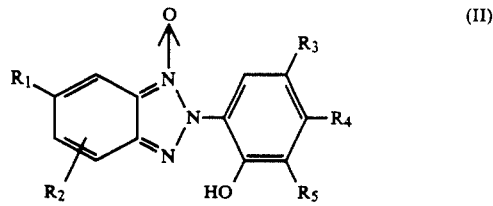

(wherein $R_1$, $R_2$, $R_3$, $R_4$ and $R_5$ are the same as defined above), characterized by reducing o-nitroazobenzenes having the general formula III,

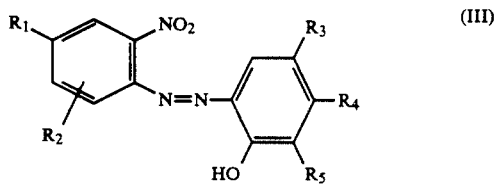

(wherein $R_1$, $R_2$, $R_3$, $R_4$ and $R_5$ are the same as defined above) with at least one of primary alcohols and secondary alcohols in the presence of an aromatic ketone compound catalyst and base.

DETAILED DESCRIPTION OF THE INVENTION

In order to solve the above mentioned problems of the conventional methods, we have variously studied and developed a catalyst, the quality of which does not change and which can be easily handled.

As the result of the study, we have found that the desired 2-phenylbenzotriazoles having the general formula I,

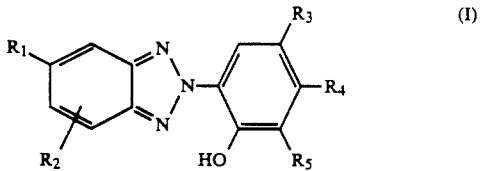

(wherein $R_1$, $R_2$, $R_3$, $R_4$ and $R_5$ are the same as defined above) can be produced with technically and economically satisfactory results without causing environmental polution, by reducing (i) o-nitroazobenzenes having the general formula III,

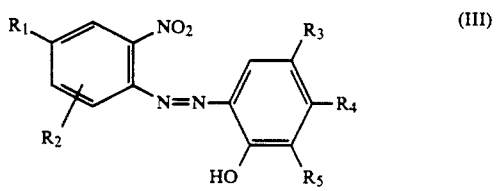

(wherein $R_1$, $R_2$, $R_3$, $R_4$ and $R_5$ are the same as defined above) or (ii) 2-phenylbenzotriazole-N-oxides having the general formula II,

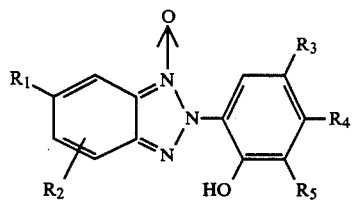

(wherein $R_1$, $R_2$, $R_3$, $R_4$ and $R_5$ are the same as defined above) with at least one of primary alcohols and secondary alcohols in the presence of an aromatic ketone compound catalyst and base.

The method (i) for preparing 2-phenylbenzotriazoles having the general formula I by reducing o-nitroazobenzenes having the general formula III in accordance with the present invention can be carried out by either one step or two steps depending on the conditions of reaction temperature, reaction time and the amount of primary and/or secondary alcohol reducing agents used as mentioned below.

(A) In the case of one step method:

The suitable reaction temperature condition for this process [Process (a)] is about 60° to 110° C., and the suitable reaction time is about 3 to 12 hours. A primary alcohol reducing agent is suitably used in an amount of about 0.9 to 1.3 moles per mole of the starting material, i.e. o-nitroazobenzenes of the general formula III, and a secondary alcohol reducing agent is suitably used in an amount of about 1.8 to 2.6 moles on the same basis.

The reaction is carried out in the following manner:

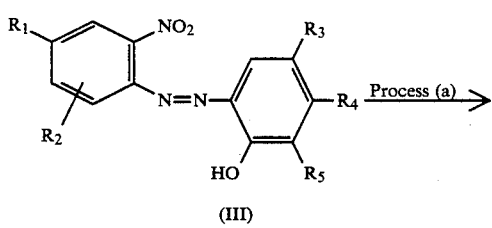

(wherein $R_1$, $R_2$, $R_3$, $R_4$ and $R_5$ are the same as defined above).

The reaction in the presence of a primary alcohol reducing agent is carried out in the following manner:

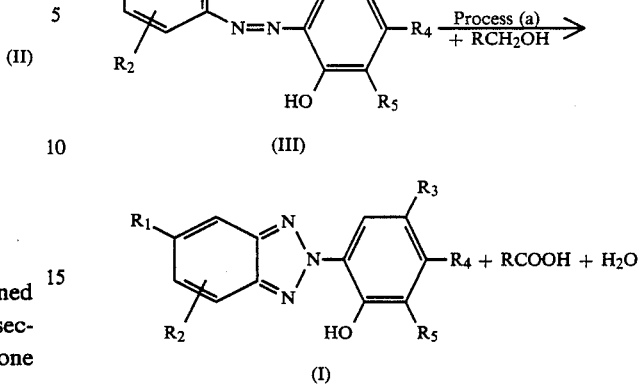

(wherein $R_1$, $R_2$, $R_3$, $R_4$ and $R_5$ are the same as defined above, and R represents hydrogen or alkyl group).

The reaction in the presence of a secondary alcohol reducing agent is carried out in the following manner.

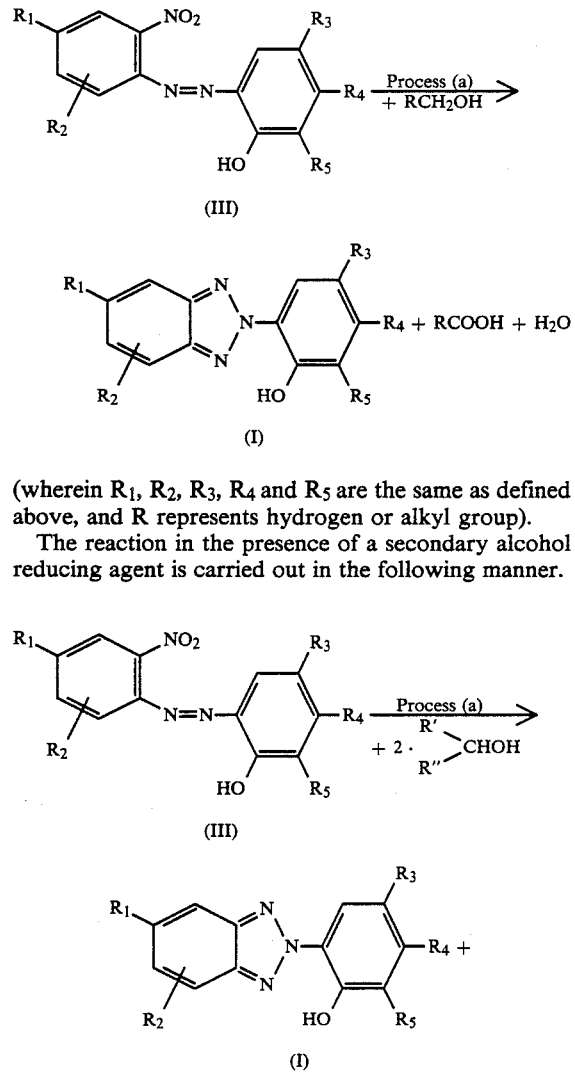

(wherein $R_1$, $R_2$, $R_3$, $R_4$ and $R_5$ are the same as defined above, and R' and R" represent the same or different alkyl group).

(B) In the case of two step method:

The reaction of the first step [Process (b)] is suitably carried out at about 60° to 100° C. for 2 to 10 hours, and the reaction of the second step [Process (c)] is suitably carried out at about 70° to 110° C. for 1 to 4 hours.

This two step method is sometimes advantageous in view of the quality of product and the yield although it takes two steps.

The first step [Process (b)] is suitably carried out by using 0.4 to 0.7 mole of a primary alcohol and/or 0.8 to 1.4 moles of a secondary alcohol per mole of the starting material, i.e. o-nitroazobenzenes of the general formula III to produce an intermediate product, and the second step [Process (c)] is suitably carried out by using 0.4 to 0.7 mole of a primary alcohol and/or 0.8 to 1.4 moles of a secondary alcohol per mole of the intermediate, i.e. 2-phenylbenzotriazole-N-oxides of the general formula II.

The reaction is carried out in the following manner.

(III) → Process (b) → (II) → Process (c) → (I)

(wherein $R_1$, $R_2$, $R_3$, $R_4$ and $R_5$ are the same as defined above).

The reaction in the presence of a primary alcohol reducing agent is carried out in the following manner:

Process (b): (III) + $RCH_2OH$ →

(II)

Process (c): (II) →

2· (II) + $RCH_2OH$ $\xrightarrow{\text{Process (c)}}$ (I) + $RCOOH + H_2O$ (wherein $R_1$, $R_2$, $R_3$, $R_4$ and $R_5$ are the same as defined above, and R represents hydrogen or alkyl group).

The reaction in the presence of a secondary alcohol reducing agent is carried out in the following manner.

Process (b): (III) + $\begin{matrix}R'\\R''\end{matrix}\!\!>\!CHOH$ →

(II) + $\begin{matrix}R'\\R''\end{matrix}\!\!>\!C=O + H_2O$

Process (c): (II) + $\begin{matrix}R'\\R''\end{matrix}\!\!>\!CHOH$ →

(I) + $\begin{matrix}R'\\R''\end{matrix}\!\!>\!C=O + H_2O$ (wherein $R_1$, $R_2$, $R_3$, $R_4$ and $R_5$ are the same as defined above, and R' and R" represent the same or different alkyl group).

The method (ii) for preparing 2-phenylbenzotriazoles of the general formula I by reducing 2-phenylbenzotriazole-N-oxides of the general formula II is carried out in quite the same manner as in the above mentioned Process (c).

In the method (iii), the desired 2-phenylbenzotriazole-N-oxides having the general formula II,

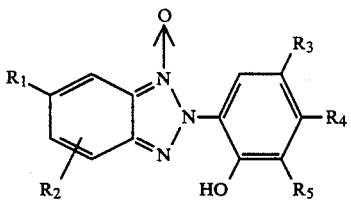

(wherein $R_1$, $R_2$, $R_3$, $R_4$ and $R_5$ are the same as defined above) can be produced with techinically and economically satisfactory results without causing environmental polution, by reducing o-nitroazobenzenes having the general formula III,

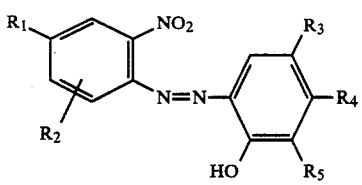

(wherein $R_1$, $R_2$, $R_3$, $R_4$ and $R_5$ are the same as defined above) with a primary and/or secondary reducing agent in the presence of an aromatic ketone compound catalyst and base.

This reaction of the method (iii) is carried out in the following manner.

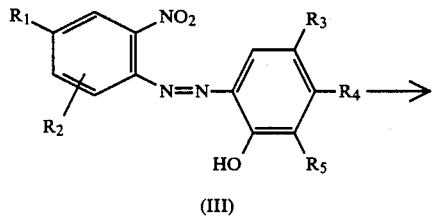

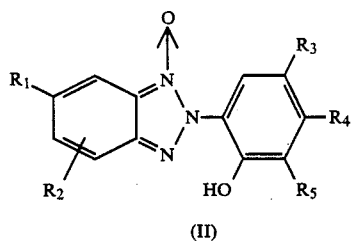

(wherein $R_1$, $R_2$, $R_3$, $R_4$ and $R_5$ are the same as defined above).

This reaction is quite the same as that of the above mentioned Process (b). This reaction is rapidly and exothermally conducted at a temperature of about 50° to 100° C.

In order to smoothly carry out the reactions of the methods (i), (ii) and (iii), all the reactions of the above mentioned Process (a), Process (b) and Process (c) are carried out in an aqueous solution, or in an inert solvent such as alcohols (the same alcohols used as a reducing agent are usable), toluene, acetone, dimethylsulfoxide, acetonitrile and the like, or in a mixture of the above mentioned inert solvent with water. If necessary, a surface active agent, a phase-transfer catalyst, and the like may be added.

Examples of o-nitroazobenzenes expressed by the general formula III used as a starting material in the methods (i) and (iii) include:
2-nitro-4-chloro-2'-hydroxy-3'-t-butyl-5'-methylazobenzene,
2-nitro-2'-hydroxy-5'-methylazobenzene,
2-nitro-2'-hydroxy-5'-t-octylazobenzene,
2-nitro-2'-hydroxy-5'-t-butylazobenzene,
2-nitro-4-chloro-2'-hydroxy-3',5'-di-t-butylazobenzene,
2-nitro-2'-hydroxy-3',5'-di-t-amylazobenzene,
2-nitro-2'-hydroxy-3',5'-di-t-butylazobenzene,
2-nitro-2'-hydroxy-3'-t-butyl-5'-methylazobenzene,
2-nitro-2',4'-dihydroxyazobenzene,
2-nitro-4-chloro-2',4'-dihydroxyazobenzene,
2-nitro-2'-hydroxy-4'-methoxyazobenzene,
2-nitro-4-chloro-2'-hydroxy-3',5'-di-t-amylazobenzene,
2-nitro-2'-hydroxy-5'-t-amylazobenzene,
2-nitro-4-chloro-2'-hydroxy-5'-t-amylazobenzene,
2-nitro-2'-hydroxy-3',5'-di($\alpha,\alpha$-dimethylbenzyl)azobenzene,
2-nitro-4-chloro-2'-hydroxy-3',5'-di($\alpha,\alpha$-dimethylbenzyl)azobenzene,
2-nitro-2'-hydroxy-3'-$\alpha$-methylbenzyl-5'-methylazobenzene,
2-nitro-4-chloro-2'-hydroxy-3'-$\alpha$-methylbenzyl-5'-methylazobenzene,
2-nitro-2'-hydroxy-5'-n-dodecylazobenzene,
2-nitro-4-chloro-2'-hydroxy-5'-n-dodecylazobenzene,
2-nitro-2'-hydroxy-3',5'-di-t-octylazobenzene,
2-nitro-4-chloro-2'-hydroxy-3',5'-di-t-octylazobenzene,
2-nitro-4-chloro-2'-hydroxy-5'-t-octylazobenzene,
2-nitro-4-methyl-2'-hydroxy-5'-methylazobenzene,
2-nitro-4-methyl-2'-hydroxy-3'-t-butyl-5-methylazobenzene,
2-nitro-4-n-butyl-2'-hydroxy-3',5'-di-t-butylazobenzene,
2-nitro-4-n-butyl-2'-hydroxy-3'-sec-butyl-5'-t-butylazobenzene,
2-nitro-4-t-butyl-2'-hydroxy-3'-sec-butyl-5'-t-butylazobenzene,
2-nitro-4,6-dichloro-2'-hydroxy-5'-t-butylazobenzene,
2-nitro-4,6-dichloro-2'-hydroxy-3',5'-di-t-butylazobenzene, and
2-nitro-4-carboxy-2'-hydroxy-5-methylazobenzene.

2-phenylbenzotriazole-N-oxides of the general formula II used in the method (ii) of the present invention can be obtained by reducing o-nitroazobenzenes of the general formula III into the N-oxides, examples of which include as follows:
2-(2-hydroxy-3-t-butyl-5-methylphenyl)-5-chlorobenzotriazole-N-oxide,
2-(2-hydroxy-3,5-di-t-butylphenyl)-5-chlorobenzotriazole-N-oxide,
2-(2-hydroxy-3,5-di-t-amylphenyl)benzotriazole-N-oxide,
2-(2-hydroxy-5-methylphenyl)benzotriazole-N-oxide,
2-(2-hydroxy-5-t-butylphenyl)benzotriazole-N-oxide,
2-(2-hydroxy-5-t-octylphenyl)benzotriazole-N-oxide,
2-(2-hydroxy-3,5-di-t-butylphenyl)benzotriazole-N-oxide,
2-(2-hydroxy-3-t-butyl-5-methylphenyl)benzotriazole-N-oxide,
2-(2,4-dihydroxyphenyl)benzotriazole-N-oxide,
2-(2,4-dihydroxyphenyl)-5-chlorobenzotriazole-N-oxide,
2-(2-hydroxy-4-methoxyphenyl)benzotriazole-N-oxide, 2-[2-hydroxy-3,5-di-(α,α-dimethylbenzyl)phenyl]benzotriazole-N-oxide, and 2-(2-hydroxy-3-α-methylbenzyl-5-metylphenyl)benzotriazole-N-oxide.

It is preferable to prepare these 2-phenyltriazole-N-oxides of the general formula II by reducing o-nitroazobenzenes of the general formula III as a starting material in accordance with the above mentioned Process (b), but these materials can also be prepared by other known methods.

Examples of alcohols used as a reducing agent in the present invention include methanol, ethanol, n-propanol, n-butanol, isobutanol, m-amyl alcohol, isoamyl alcohol, n-hexanol, 2-ethylbutanol, n-heptyl alcohol, n-octanol, 2-ethylhexanol, 3,5,5-trimethyl hexanol, n-decanol, dodecanol, tetradecanol, isopropyl alcohol, secondary butanol, 3-pentanol, methylamyl alcohol, 2-heptanol, 3-heptanol, 2-octanol, nonanol, undecanol and the like. Among them, n-propanol, n-butanol, n-amyl alcohol, isopropyl alcohol, secondary butanol, secondary amyl alcohol and n-octanol are preferable.

These alcohol reducing agents are used preferably in an amount more than a stoichiometric amount. Generally, alcohols are used also as a solvent, and accordingly they are used in a weight amount of 1 to 20 times, preferably 2 to 8 times larger than the amount of the starting material, i.e. o-nitroazobenzenes of the general formula III or 2-phenylbenzotriazole-N-oxides of the general formula II.

These alcohol reducing agents may be used in a mixture of two or more, and the combination use sometimes brings a good result.

These alcohols may be used as an aqueous solution, and in such a case, the concentration of alcohol in the aqueous solution should preferably be at least 50% by weight. The fact that alcohols can be used in an aqueous solution brings a great advantage in view of the industrial production that the recovered alcohols can be reused without being dehydrated.

Examples of an aromatic ketone compound catalyst include benzophenone; benzophenone substituted with alkyl group, alkoxyl group, halogen atom or hydroxyl group; benzanthrone; 9-fluorenone; 9-xanthenone; and the like. Among them, preferable examples include 9-fluorenone and benzathrone.

These aromatic ketone catalysts may be used alone or in a mixture of two or more. It is sometimes more preferable to use them in a mixture of two or more.

In any case of the above mentioned Processes (a), (b) and (c), an aromatic ketone catalyst is used generally in an amount of 0.2 to 30%, preferably 2 to 20% on the basis of the weight of the starting material, i.e. o-nitroazobenzenes or 2-phenylbenzotriazole-N-oxides.

The above mentioned aromatic ketone catalysts are generally soluble in an organic solvent such as benzene, toluene, xylene, alcohols and the like, and have a boiling point. Accordingly, the used aromatic ketone catalysts can easily be recovered from the reaction system by extraction distillation. The recovered catalysts can be reused for the next reaction, thus the semipermanent use of the catalyst being possible. This is also one of the advantages of the present invention.

Examples of the base used in the present invention include sodium hydroxide, potassium hydroxide and the like. The base is used in an amount of 1 to 12 moles, preferably 2 to 8 moles per one mole of the starting material, i.e. o-nitroazobenzenes or 2-phenylbenzotriazole-N-oxides.

The present invention is further illustrated by the following Examples, but is not limited thereto.

EXAMPLE 1

2-nitro-2'-hydroxy-3',5'-di-t-amylazobenzene 25.5 g was added to a mixture of n-butanol 80 g, water 14 g and 97% sodium hydroxide 8.2 g, and the resultant mixure was stirred while raising temperature to 65° C. Thereafter, the mixture was cooled to 50° C., and 9-fluorenone 2.0 g was added to the mixture. The reaction mixture was then heated to 90° C. in one hour, and the mixture was stirred at 90°~96° C. for four hours to effect reaction, thus almost all of the azobenzene having disappeared. Thereafter, water 50 ml was added to the reaction liquor, and the reaction liquor was neutralized to pH 8~9 with 62% sulfuric acid 13 g to precipitate a crystal. The crystal thus obtained was filtered to separate the crystal, and the separated crystal was then fully washed with water and further with a small amount of methanol. The washed crystal was then dried, thus producing 23.2 g of 2-(2-hydroxy-3',5'-di-t-amylphenyl)benzotriazole-N-oxide having a melting point of 111° to 113° C. at the yield of 95.0%.

EXAMPLE 2

The same procedure as in Example 1 was repeated, except that 2-nitro-2'-hydroxy-3',5'-di-t-amylazobenzene 25.5 g was replaced by 2-nitro-2'-hydroxy-5'-t-octylazobenzene 23.7 g, thus producing 20.3 g of 2-(2-hydroxy-5-t-octylphenyl)benzotriazole-N-oxide having a melting point of 106° to 110° C. at the yield of 90.0%.

EXAMPLE 3

The same procedure as in Example 1 was repeated, except that n-butanol 80 g was replaced by n-propanol 80 g, and that 2-nitro-2'-hydroxy-3',5'-di-t-amylazobenzene 25.5 g was replaced by 2-nitro-2'-hydroxy-5-methylazobenzene 17.1 g, thus producing 14.1 g of 2-(2-hydroxy-5-methylphenyl)benzotriazole-N-oxide having a melting point of 138° to 140° C. at the yield of 88%.

EXAMPLE 4

The same procedure as in Example 1 was repeated, except that 9-fluorenone was replaced respectively by (a) benzanthrone 2.0 g and (b) benzophenone 2.0 g, thus producing 2-(2-hydroxy-3,5-di-t-amylphenyl)benzotriazole-N-oxide having a melting point of 110° to 113° C. at the yields respectively of (a) 20.8 g, 85% and (b) 15.9 g, 65%.

EXAMPLE 5

2-nitro-4-chloro-2'-hydroxy-3'-t-butyl-5'-methylazobenzene 23.2 g was added to a mixture of n-butanol 60 g, water 10.6 g and 97% sodium hydroxide 6.9 g, and the resultant mixture was stirred while raising temperature to 65° C. Thereafter, the mixture was cooled to 50° C., and 9-fluorenone 1.5 g was added to the mixture. The reaction mixture was then heated to 90° C. in one hour, and the mixture was stirred at 90°~96° C. for five hours to effect reaction, thus almost all of the azobenzene having disappeared. Thereafter, water 50 ml was added to the reaction liquor, and the reaction liquor was neutralized to pH 8~9 with 62% sulfuric acid 10 g to precipitate a crystal. The crystal thus obtained was filtered to separate the crystal, and the separated crystal was then fully washed with water and further with a small amount of methanol. The washed crystal was then dried, thus producing 20.6 g of 2-(2-hydroxy-3-t-butyl-5-methylphenyl)-5-chlorobenzotriazole-N-oxide having a melting point of 160° to 163° C. at the yield of 93.0%.

EXAMPLE 6

2-nitro-4-chloro-2'-hydroxy-3',5'-di-t-butylazobenzene 26.0 g and 9-fluorenone 2.0 g were added to a mixture of isopropyl alcohol 80 g, water 14 g and 97% sodium hydroxide 11.0 g, and the resultant mixture was stirred at the boiling point of 79° C. for 8 hours to effect reaction, thus almost all of the azobenzene having disappeared.

Thereafter, water 50 ml was added to the reaction liquor, and the reaction liquor was neutralized to pH 8~9 with 62% sulfuric acid 21 g. The neutralized reaction liquor was cooled to 20° C. to precipitate a crystal. The crystal thus obtained was filtered to separate the crystal, and the separated crystal was then fully washed with water and further with a small amount of isopropyl alcohol. The washed crystal was then dried, thus producing 21.9 g of 2-(2-hydroxy-3,5-di-t-butylphenyl)-5-chlorobenzotriazole-N-oxide having a melting point of 178° to 180° C. at the yield of 88.0%.

EXAMPLE 7

2-nitro-2'-hydroxy-5'-t-butylazobenzene 19.9 g was added to a mixture of secondary butanol 80 g, water 14 g and 97% sodium hydroxide 11.2 g, and the resultant mixture was stirred while raising temperature to 65° C. Thereafter, the mixture was cooled to 50° C., and 9-fluorenone 1.5 g was added to the mixture. The reaction mixture was then stirred at 90°~95° C. for five hours to effect reaction, thus almost all of the azobenzene having disappeared. Thereafter, water 50 ml was added to the reaction liquor, and the reaction liquor was neutralized to pH 8 with 62% sulfuric acid 15 g. The neutralized reaction liquor was then cooled to 20° C. or lower to precipitate a crystal. The crystal thus obtained was filtered to separate the crystal, and the separated crystal was then fully washed with water and further with a small amount of methanol. The washed crystal was then dried, thus producing 15.5 g of 2-(2-hydroxy-5-t-butylphenyl)benzotriazole-N-oxide having a melting point of 95° to 98° C. at the yield of 82.0%.

EXAMPLE 8

The same procedure as in Example 7 was repeated, except that secondary butanol 80 g was replaced by n-octanol 50 g, and that 2-nitro-2'-hydroxy-5'-t-butylazobenzene 19.9 g was replaced by 2-nitro-2'-hydroxy-3',5'-di-t-butylazobenzene 23.7 g, thus producing 18.7 g of 2-(2-hydroxy-3,5-di-t-butylphenyl)benzotriazole-N-oxide having a melting point of 168° to 171° C. at the yield of 83.0%.

EXAMPLE 9

2-nitro-2'-hydroxy-3',5'-di-t-amylazobenzene 25.5 g was added to a mixture of n-butanol 80 g, water 14 g and 97% sodium hydroxide 8.2 g, and the resultant mixture was stirred while raising temperature to 65° C. Thereafter, the mixture was cooled to 50° C., and 9-fluorenone 2.0 g was added to the mixture. The reaction mixture was then heated to 90° C. in one hour, and the mixture was stirred at 90°~96° C. for four hours to effect reaction, thus almost all of the azobenzene having disappeared to produce 2-(2-hydroxy-3,5-di-t-amylphenyl)benzotriazole-N-oxide. Thus, the reaction of Process (b) was finished.

In order to further conduct the reaction of Process (c), the resultant reaction liquor was cooled to 60° C., and 97% sodium hydroxide 8.2 g and 9-fluorenone 1.0 g were added to the reaction liquor. The reaction mixture was then heated to 90° C. in one hour, and was further stirred at 90°~97° C. for two hours, thus the N-oxide having disappeared to complete the reaction of Process (c). Thereafter, water 80 ml was added to the reaction liquor, and the reaction liquor was then neutralized to pH 8~9 with 62% sulfuric acid 26.0 g. The neutralized reaction liquor was then allowed to stand at 60°~70° C. to form a butanol layer containing 2-(2-hydroxy-3,5-di-t-amylphenyl)benzotriazole as the upper layer and an aqueous layer as the lower layer. After removing the lower aqueous layer, the upper butanol layer was placed in a distillation apparatus, and the most of butanol was recovered under normal pressure or a slightly reduced pressure. Thereafter, the system was subjected to vacuum state of 2~4 mmHg to recover 2.9 g of a fraction of 120°~140° C. The recovered fraction was 9-fluorenone used as a catalyst, and 9-fluorenone can be reused as a catalyst for the next process. After removing the catalyst, the remaining material was washed with methanol to produce the final product, i.e. 2-(2-hydroxy-3,5-di-t-amylphenyl)benzotriazole 20.0 g having a melting point of 78°~80° C. at the yield of 85.4%.

EXAMPLE 10

The same procedure as in Example 9 was repeated, except that 2-nitro-2'-hydroxy-3',5'-di-t-amylazobenzene 25.5 g was replaced by 2-nitro-2'-hydroxy-5'-t-octylazobenzene 23.7 g. Thus, after recovering the catalyst, the remaining material was washed with methanol to produce 18.0 g of 2-(2-hydroxy-5-t-octylphenyl)benzotriazole having a melting point of 103° to 105° C. at the yield of 83.7%.

EXAMPLE 11

The same procedure as in Example 9 was repeated, except that n-butanol 80 g was replaced by n-propanol 80 g. The desired product could be obtained at quite the same yield as in Example 9. 9-fluorenone used in this Example was those recovered in Examples 9 and 10.

EXAMPLE 12

The same procedure as in Example 9 was repeated, except that 9-fluorenone was replaced respectively by (a) benzanthrone and (b) benzophenone. 2-(2-hydroxy-3,5-di-t-amylphenyl)benzotriazole could be obtained respectively at the following yields.
(a) 19.4 g, Yield: 83%, Melting Point: 77°~80° C.
(b) 14.3 g, Yield: 61%, Melting Point: 76°~79° C.

EXAMPLE 13

2-nitro-4-chloro-2'-hydroxy-3'-t-butyl-5'-methylazobenzene 23.2 g was added to a mixture of n-butanol 60 g, water 10.6 g and 97% sodium hydroxide 6.9 g, and the resultant mixture was stirred while raising temperature to 65° C. Thereafter, the mixture was cooled to 50° C., and 9-fluorenone 1.5 g was added to the mixture. The reaction mixture was then heated to 90° C. in one hour, and the mixture was stirred at 90°~96° C. for five hours to effect reaction, thus almost all of the azobenzene having disappeared to finish the reaction of Process (b). Thereafter, water 50 ml was added to the reaction mixture, and the mixture was neutralized to pH 8~9 with 62% sulfuric acid 10 g. The neutralized liquor was cooled to 20° C. to precipitate a crystal. The crystal thus precipitated was separated by filtration, thus producing the wet product 22.9 g of 2-(2-hydroxy-3-t-butyl-5-methylphenyl)-5-chlorobenzotriazole-N-oxide (dry product: 20.6 g, yield: 93.0%, melting point: 160°~163° C.).

The wet product thus prepared was added to a mixture of 90% n-butanol 66.7 g, 97% sodium hydroxide 16.5 g, and 9-fluorenone 1.5 g. The resultant mixture was heated to 90° C. in one hour, and was reacted at 90° to 97° C. for 3 hours, thus the N-oxide having disappeared to finish the reaction of Process (c).

After adding water 80 ml to the above prepared reaction liquor, the resultant reaction liquor was neutralized to pH 8~9 with 62% sulfuric acid 28 g to precipitate a crystal. The neutralized liquor was cooled to 20° C. to precipitate a crystal. The crystal thus obtained was separated by filtration, and the separated crystal was fully washed with water and further with a small amount of methanol. The washed crystal was then dried, thus producing a light yellow crystal 18.2 g of 2-(2-hydroxy-3-t-butyl-5-methylphenyl)-5-chlorobenzotriazole having a melting point of 139° to 140° C. at the yield of 87% (on the basis of azobenzene).

After filtering the N-oxide and the final product, the used catalyst can be recovered by allowing the filtrate to stand, thus the butanol layer being separated. The butanol layer thus separated is placed in a distillation apparatus. After recovering butanol, a fraction of 120°~140° C. was taken out under vacuum of 2~4 mmHg, thus recovering 80% or more of the used catalyst.

EXAMPLE 14

2-nitro-4-chloro-2'-hydroxy-3',5'-di-t-butylazobenzene 26.0 g and 9-fluorenone 2.0 g were added to a mixture of isopropyl alcohol 80 g, water 14 g and 97% sodium hydroxide 11.0 g, and the resultant mixture was stirred at the boiling point of 79° C. for 8 hours to effect reaction, thus almost all of the azobenzene having disappeared to produce 2-(2-hydroxy-3,5-di-t-butylphenyl)-5-chlorobenzotriazole-N-oxide. Thus, the reaction of Process (b) was completed.

Thereafter, in order to further effect the reaction of Process (c), the reaction liquor was cooled to 60° C., and 97% sodium hydroxide 8.2 g and then 9-fluorenone 1.0 g were added to the reaction liquor. The resultant reaction liquor was stirred at the boiling point (79°~82° C.) for 6 hours, thus the N-oxide having disappeared to complete the reaction of Process (c).

Thereafter, water 80 ml was added to the reaction liquor, and the reaction liquor was neutralized to pH 8~9 with 62% sulfuric acid 36 g. The neutralized liquor was cooled to 20° C. to precipitate a crystal. The crystal thus precipitated was separated by filtration, and the separated crystal was washed with water and further with a small amount of isopropyl alcohol. The washed crystal was dried, thus producing 18.6 g of 2-(2-hydroxy-3,5-di-t-butylphenyl)-5-chlorobenzotriazole having a melting point of 153°~155° C. at the yield of 78%.

EXAMPLE 15

9-fluorenone 2.5 g was added to a mixture of secondary butanol 80 g, water 14 g and 97% sodium hydroxide 22.4 g, and 2-nitro-2'-hydroxy-5'-t-butylazobenzene 19.9 g was added to the resultant mixture for one hour while stirring at 80° C. The mixture was further stirred at 90°~97° C. for 4 hours, thus almost all of the azobenzene having disappeared to produce 2-(2-hydroxy-5-t-butylphenyl)benzotriazole-N-oxide. Thus, the reaction of Process (b) was completed. The resultant reaction liquor was further stirred for 4 hours, thus the N-oxide having disappeared to finish the reaction of Process (c).

After adding water 80 ml to the resultant reaction liquor, the liquor was distilled to recover an excess amount of secondary butanol. Toluene 50 ml was then added to the remaining liquor, and the liquor was neutralized to pH 8 with 62% sulfuric acid 31 g. The neutralized liquor was allowed to stand at 70° C., and the liquor was separated into the toluene layer containing the desired product as the upper layer and an aqueous layer containing sodium sulfate as the lower layer. The upper toluene layer was placed in a distillation apparatus, and most of toluene was removed by distillation under normal pressure. Thereafter, a fraction 2.5 g at 120°~140° C. was recovered under vacuum of 2~4 mmHg. The fraction thus obtained was the used catalyst, 9-fluorenone, and the catalyst thus recovered can be reused for the next process. After recovering the catalyst, the desired product, i.e. 13.5 g of 2-(2-hydroxy-5-t-butylphenyl)benzotriazole having a melting point of 96°~98° C. was obtained at the yield of 76%.

EXAMPLE 16

2-nitro-2'-hydroxy-3',5'-di-t-butylazobenzene 23.7 g was added to a mixture of n-octanol 50 g, water 14 g and 97% sodium hydroxide 8.2 g, and the resultant mixture was heated to 65° C. The mixture was then cooled to 50° C., and 9-fluorenone 2.0 g was added thereto. The resultant mixture was stirred at 90°~97° C. for 2 hours, thus almost all of the azobenzene having disappeared to produce 2-(2-hydroxy-3,5-di-t-butylphenyl)benzotriazole-N-oxide. Thus, the reaction of Process (b) was completed.

Thereafter, in order to further effect the reaction of Process (c), the reaction liquor was cooled to 60° C., and 97% sodium hydroxide 8.2 g and then 9-fluorenone 1.0 g were added to the reaction liquor. The resultant reaction liquor was raised to 90° C. and stirred at 90°~97° C. for 2 hours, thus the N-oxide having disappeared to complete the reaction of Process (c).

Thereafter, water 80 ml was added to the reaction liquor, and the reaction liquor was neutralized to pH 8~9 with 62% sulfuric acid 26 g. The neutralized liquor was cooled to 20° C. to precipitate a crystal. The crystal thus precipitated was separated by filtration, and the separated crystal was fully washed with water and further with a small amount of methanol. The washed crystal was dried, thus producing 17.0 g of 2-(2-hydroxy-3,5-di-t-butylphenyl)benzotriazole having a melting point of 150°~152° C. at the yield of 79%.

EXAMPLE 17

2-nitro-2'-hydroxy-5'-t-octylazobenzene 23.7 g was added to a mixture of n-butanol 60 g, water 12 g and 97% sodium hydroxide 16.5 g, and the resultant mixture was heated to 50° C. while stirring. 9-fluorenone 2.0 g was added to the mixture, and the resultant mixture was heated to 80° C. in two hours. The mixture was then stirred at 80°~84° C. for 3.5 hours, thus the reduction reaction being completed.

After adding water 80 ml to the resultant reaction liquor, the liquor was neutralized to pH 8 with 62% sulfuric acid 28 g. The neutralized liquor was allowed to stand at 60°~70° C., and the liquor was separated into the butanol layer containing the desired product, i.e.

2-(2-hydroxy-5-t-octylphenyl)benzotriazole as the upper layer and an aqueous layer as the lower layer. After removing the lower aqueous layer, the upper butanol layer was placed in a distillation apparatus, and most of butanol was recovered by distillation under normal pressure or slightly reduced pressure. Thereafter, a fraction 1.8 g at 120°~140° C. was recovered under vacuum of 2~3 mmHg. The fraction thus obtained was the used catalyst, i.e. 9-fluorenone, and the catalyst thus recovered can be reused for the next step. After recovering the catalyst, the remaining material was washed with methanol to produce the desired product, i.e. 17.4 g of 2-(2-hydroxy-5-t-octylphenyl)benzotriazole having a melting point of 103°~105° C. was obtained at the yield of 81.0%.

EXAMPLE 18

2-(2-hydroxy-3,5-di-t-amylphenyl)benzotriazole-N-oxide 23.2 g was added to a mixture of n-butanol 60 g, water 12 g and 97% sodium hydroxide 16.5 g, and 9-fluorenone 2.0 g was further added to the resultant mixture. The resultant mixture was heated to 80° C., and was further stirred at 80°~85° C. for 2.5 hours, thus the reduction reaction being completed. The reaction liquor was treated in the same manner as in Example 17 to recover butanol, and 1.8 g of 9-fluorenone catalyst was recovered as a fraction at 120°~130° C. under vacuum of 2~3 mmHg. After recovering the catalyst, the remaining material was washed with methanol to produce the desired product, i.e. 20.5 g of 2-(2-hydroxy-3,5-di-t-amylphenyl)benzotriazole having a melting point of 79°~80° C. at the yield of 92.8%.

What we claim is:

1. A method for preparing a 2-phenyl-benzotriazole of formula I,

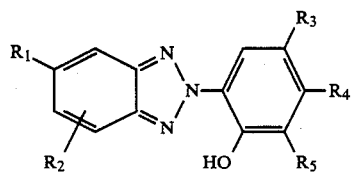
(I)

wherein $R_1$ represents hydrogen, chlorine, a lower alkyl group having a carbon number of 1 to 4, a lower alkoxy group having a carbon number of 1 to 4, carboxyl group or a sulfonic acid group; $R_2$ represents hydrogen, chlorine, a lower alkyl group having a carbon number of 1 to 4, or a lower alkoxy group having a carbon number of 1 to 4; $R_3$ represents hydrogen, chlorine, an alkyl group having a carbon number of 1 to 12, a lower alkoxy group having a carbon number of 1 to 4, a phenyl group, a phenyl group substituted with an alkyl group which has a carbon number of 1 to 8, a phenoxy group or a phenylalkyl group, the alkyl portion of which having a carbon number of 1 to 4; $R_4$ represents hydrogen, chlorine, hydroxy group, or a lower alkoxy group having a carbon number of 1 to 4; and $R_5$ represents hydrogen, an alkyl group having a carbon number of 1 to 12, or a phenylalkyl group, the alkyl part of which having a carbon number of 1 to 4 comprising: reducing an o-nitroazobenzene of formula III,

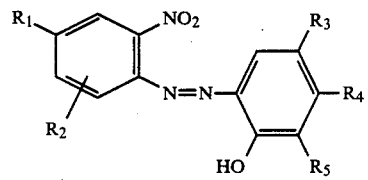
(III)

wherein $R_1$, $R_2$, $R_3$, $R_4$ and $R_5$ are as defined above with an alcohol reducing agent of at least one selected from the group consisting of primary and secondary alcohol reducing agents, said primary alcohol reducing agent used in an amount of 0.9 to 1.3 mole primary alcohol reducing agent to each mole of o-nitroazobenzene and said secondary alcohol reducing agent used in an amount of 1.8 to 2.6 mole secondary alcohol reducing agent to each mole of o-nitroazobenzene, said reducing step carried out in the presence of an aromatic ketone catalyst, selected from the group consisting of benzanthrone and 9-fluorenone and a base to form said 2-phenylbenzotriazole by reaction of the compound of formula III with said alcohol reducing agent.

2. A method according to claim 1, wherein said alcohol reducing agent is at least one selected from the group consisting of a methanol, an ethanol, an n-propanol, an n-butanol, an isobutanol, an n-amyl alcohol, an isoamyl alcohol, an n-hexanol, a 2-ethylbutanol, an n-heptyl alcohol, an n-octanol, a 2-ethylhexanol, a 3,5,5-trimethyl hexanol, an n-decanol, a dodecanol, a tetradecanol, an isopropyl alcohol, a secondary butanol, a 3-pentanol, a methylamyl alcohol, a 2-heptanol, a 3-heptanol, a 2-octanol, a nonanol, and an undecanol.

3. A method according to claim 1 comprising: using 0.2 to 30% by weight of said aromatic ketone catalyst to said o-nitroazobenzene of formula III.

4. A method according to claim 1, comprising using 1 to 12 moles of said base to each mole of said o-nitroazobenzene.

5. A method according to claim 4, wherein said base is at least one selected from the group consisting of a sodium hydroxide and a potassium hydroxide.

6. A method according to claim 1, comprising carrying out the method at about 60° to 110° C. for about 3 to 12 hours.

7. A method for preparing a 2-phenylbenzotriazole of formula I,

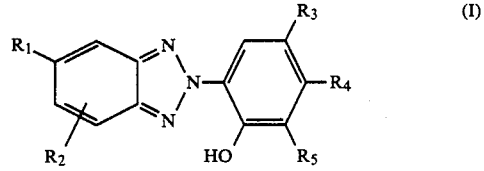
(I)

wherein $R_1$ represents hydrogen, chlorine, a lower alkyl group having a carbon number of 1 to 4, a lower alkoxy group having a carbon number of 1 to 4, carboxyl group or a sulfonic acid group; $R_2$ represents hydrogen, chlorine, a lower alkyl group having a carbon number of 1 to 4, or a lower alkoxy group having a carbon number of 1 to 4; $R_3$ represents hydrogen, chlorine, an alkyl group having a carbon number of 1 to 12, a lower alkoxy group having a carbon number of 1 to 4, a phenyl group, a phenyl group substituted with an alkyl group which has a carbon number of 1 to 8, a phenoxy group or a phenylalkyl group, the alkyl portion of which having a carbon number of 1 to 8, a phenoxy group or a phenylalkyl group, the alkyl portion of which having a carbon number of 1 to 4; R$_4$ represents hydrogen, chlorine, hydroxy group, or a lower alkoxy group having a carbon number of 1 to 4; and R$_5$ represents hydrogen, an alkyl group having a carbon number of 1 to 12, or a phenylalkyl group, the alkyl part of which having a carbon number of 1 to 4 comprising: reducing a 2-phenylbenzotriazole-N-oxide of formula II,

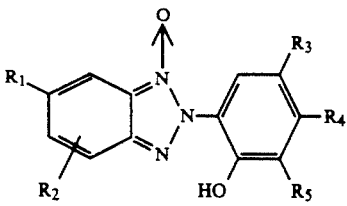

wherein R$_1$, R$_2$, R$_3$, R$_4$ and R$_5$ are as defined above with an alcohol reducing agent of at least one selected from the group consisting of primary and secondary alcohol reducing agents, said primary alcohol reducing agent used in an amount of 0.4 to 0.7 mole primary alcohol reducing agent to each mole of 2-phenylbenzotriazole-N-oxide and said secondary alcohol reducing agent used in an amount of 0.8 to 1.4 mole secondary alcohol reducing agent to each mole of 2-phenylbenzotriazole-N-oxide, said reducing step carried out in the presence of an aromatic ketone catalyst selected from the group consisting of benzanthrone and 9-fluorenone and a base to form said 2-phenylbenzotriazole by reaction of the compound of formula II with said alcohol reducing agent.

8. A method according to claim 7 wherein said alcohol reducing agent is at least one selected from the group consisting of a methanol, an ethanol, an n-propanol, an n-butanol, an isobutanol, an n-amyl alcohol, an isoamyl alcohol, an n-hexanol, a 2-ethylbutanol, an n-heptyl alcohol, an n-octanol, a 2-ethylhexanol, a 3,5,5-trimethyl hexanol, an n-decanol, a dodecanol, a tetradecanol, an isopropyl alcohol, a secondary butanol, a 3-pentanol, a methylamyl alcohol, a 2-heptanol, a 3-heptanol, a 2-octanol, a nonanol, and an undecanol.

9. A method according to claim 7 comprising using 0.2 to 30% by weight of said aromatic ketone catalyst to said 2-phenylbenzotriazole-N-oxide of formula II.

10. A method according to claim 7, comprising: using 1 to 12 moles of said base to each mole of said 2-phenylbenzotriazole-N-oxide of formula II.

11. A method according to claim 10, wherein said base is at least one selected from the group consisting of a sodium hydroxide and a potassium hydroxide.

12. A method according to claim 7 comprising: carrying out the method at about 60° to 100° C. for 2 to 10 hours.

13. A method for preparing a 2-phenylbenzotriazole-N-oxide of formula II,

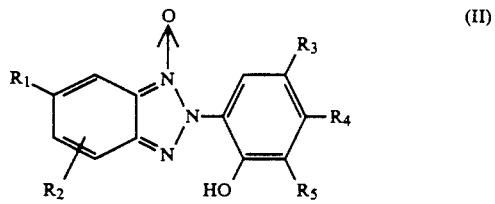

wherein R$_1$ represents hydrogen, chlorine, a lower alkyl group having a carbon number of 1 to 4, a lower alkoxy group having a carbon number of 1 to 4, carboxyl group or a sulfonic acid group; R$_2$ represents hydrogen, chlorine, a lower alkyl group having a carbon number of 1 to 4, or a lower alkoxy group having a carbon number of 1 to 4; R$_3$ represents hydrogen, chlorine, an alkyl group having a carbon number of 1 to 12, a lower alkoxy group having a carbon number of 1 to 4, a phenyl group, a phenyl group substituted with an alkyl group which has a carbon number of 1 to 8, a phenoxy group or a phenylalkyl group, the alkyl portion of which having a carbon number of 1 to 4; R$_4$ represents hydrogen, chlorine, hydroxy group, or a lower alkoxy group having a carbon number of 1 to 4; and R$_5$ represents hydrogen, an alkyl group having a carbon number of 1 to 12, or a phenylalkyl group, the alkyl part of which having a carbon number of 1 to 4 comprising: reducing an o-nitroazobenzene of formula III,

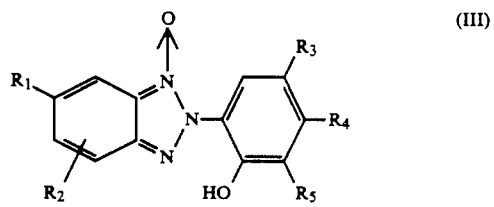

wherein R$_1$, R$_2$, R$_3$, R$_4$ and R$_5$ are as defined above with an alcohol reducing agent of at least one selected from the group consisting of primary and secondary alcohol reducing agents, said primary alcohol reducing agent used in an amount of 0.4 to 0.7 mole primary alcohol reducing agent to each mole of o-nitroazobenzene of formula III and said secondary alcohol reducing agent used in an amount of 0.8 to 1.4 mole secondary alcohol reducing agent to each mole of o-nitroazobenzene of formula III, said reducing step carried out in the presence of an aromatic ketone catalyst selected from the group consisting of benzanthrone and 9-fluorenone and a base to form said 2-phenylbenzotriazole-N-oxide by reaction of the compound of formula III with said alcohol reducing agent.

14. A method according to claim 1, wherein said alcohol reducing agent is at least one selected from the group consisting of a methanol, an ethanol, an n-propanol, an n-butanol, an isobutanol, an n-amyl alcohol, an isoamyl alcohol, an n-hexanol, a 2-ethylbutanol, an n-heptyl alcohol, an n-octanol, a 2-ethylhexanol, a 3,5,5-trimethyl hexanol, an n-decanol, a dodecanol, a tetradecanol, an isopropyl alcohol, a secondary butanol, a 3-pentanol, a methylamyl alcohol, a 2-heptanol, a 3-heptanol, a 2-octanol, a nonanol, and an undecanol.

15. A method according to claim 13 comprising: using 0.2 to 30% by weight of said aromatic ketone catalyst to said o-nitroazobenzene of formula III.

16. A method according to claim 13 comprising: using 1 to 12 moles of said base to each mole of said o-nitroazobenzene.

17. A method according to claim 13 wherein said base is at least one selected from the group consisting of a sodium hydroxide and a potassium hydroxide.

18. A method according to claim 13 comprising: carrying out the method at about 70° to 110° C. for about 1 to 4 hours.

* * * * *